United States Patent [19]

Gaertner et al.

[11] 4,221,583

[45] Sep. 9, 1980

[54] N-PHOSPHONOMETHYLGLYCINONITRILE AND CERTAIN DERIVATIVES THEREOF

[75] Inventors: Van R. Gaertner, Ballwin; Wendell G. Phillips, Manchester, both of Mo.

[73] Assignee: Monsanto Company, St. Louis, Mo.

[21] Appl. No.: 972,545

[22] Filed: Dec. 22, 1978

[51] Int. Cl.$^2$ .................. C07C 121/42; A01N 9/36; C07C 120/00
[52] U.S. Cl. .................. 71/86; 260/465 E; 260/465.5 R; 260/465.5 A; 260/940
[58] Field of Search ............ 260/940, 465.5 R, 465 E, 260/465.5 A; 71/86

[56] References Cited

U.S. PATENT DOCUMENTS

| | | | |
|---|---|---|---|
| 2,205,995 | 6/1940 | Ulrich et al. | 260/465.5 A |
| 3,923,877 | 12/1975 | Barton | 260/502.5 |
| 4,008,296 | 2/1977 | Barton | 260/940 |
| 4,067,719 | 1/1978 | Dutra | 71/86 |
| 4,083,898 | 4/1978 | Dutra | 260/970 |

FOREIGN PATENT DOCUMENTS 53-56620  5/1978  Japan .

*Primary Examiner*—Joseph Paul Brust
*Attorney, Agent, or Firm*—Arnold H. Cole; Donald W. Peterson

[57] ABSTRACT

N-phosphonomethylglycinonitrile and certain derivatives thereof are novel compounds which can be used as herbicides themselves and/or can be converted to known herbicides. Such novel compounds, and others, can be prepared by a novel process.

20 Claims, No Drawings

N-PHOSPHONOMETHYLGLYCINONITRILE AND CERTAIN DERIVATIVES THEREOF

This invention relates to a class of novel organic chemical compounds. It also relates to a novel process for preparing such compounds, and that process can also be employed to prepare certain known derivatives of such compounds. More particularly, the invention is concerned with N-phosphonomethylglycinonitrile, salts thereof and N-alkyl analogs. The invention is further concerned with the preparation of these novel materials by a Mannich type reaction which can also be used to produce known ester derivatives of the free acid glycinonitrile. The compounds prepared herein have been found to possess useful post-emergent herbicidal activity and/or they can be converted to known herbicidally active materials.

U.S. Pat. Nos. 3,923,877 and 4,008,296 describe the reaction of a dihydrocarbylphosphite with 1,3,5-tricyanomethylhexahydro-1,3,5-triazine in the presence of an acidic catalyst to produce a diester of N-phosphonomethylglycinonitrile. This product is then hydrolyzed to N-phosphonomethylglycine, a known herbicide. U.S. Pat. Nos. 4,067,719 and 4,083,898 describe the preparation of diaryl esters of N-phosphonomethylglycinonitrile using a corresponding phosphite diester and the same triazine without the need for a catalyst. Hydrolysis of the diesters to monoesters is also described, as well as the hydrolysis of such esters to N-phosphonomethylglycine.

Attempts to prepare the free acid glycinonitrile by hydrolysis of its mono or diester have been unsuccessful. This is believed to be due to the fact that the nitrile group on the molecule is more reactive than the second ester group whereby the above-mentioned N-phosphonomethylglycine is obtained rather than the sought after nitrile.

It has now been found, however, that said free acid glycinonitrile, and certain derivatives thereof, can be obtained by use of a Mannich type reaction. The novel compounds of the present invention can be illustrated by the formula

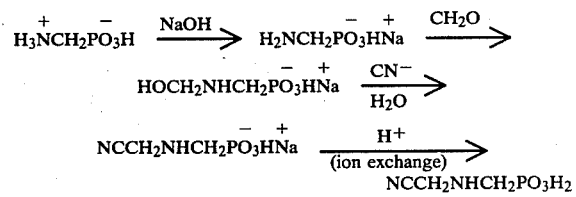

wherein R represents hydrogen or lower alkyl, X represents hydrogen and X' represents hydrogen or an agriculturally acceptable cation. As employed herein, the term "lower" designates those radicals which contain from 1 to 4 carbon atoms. The agriculturally acceptable cations are those which are commonly used in herbicidal formulations to form the salt of a free acid including, but not limited to, metals of Groups I and II having an atomic number no greater than 30, ammonium, and aliphatic ammonium cations. It will be understood that where the cation is a divalent metal, the resultant salt is formed with two molecules of the free acid, and can be represented as either

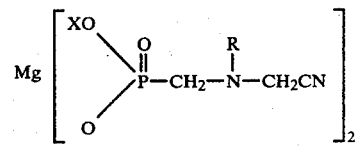

or X' = ½ Mg.

The general reaction scheme of the novel process of this invention can be illustrated as follows using aminomethylphosphonic acid as the starting material, it being understood that esters or N-substituted derivatives can also be used.

$$\overset{+}{H_3N}CH_2PO_3\overset{-}{H} \xrightarrow{NaOH} \overset{-}{H_2N}CH_2PO_3H\overset{+}{Na} \xrightarrow{CH_2O}$$
$$HOCH_2\overset{+}{N}HCH_2PO_3H\overset{+}{Na} \xrightarrow[H_2O]{CN^-}$$
$$NCCH_2\overset{+}{N}HCH_2PO_3H\overset{+}{Na} \xrightarrow[\text{(ion exchange)}]{H^+}$$
$$NCCH_2NHCH_2PO_3H_2$$

The aminomethylphosphonic acid is first treated with an alkali metal hydroxide to give the salt, and the pH at this point is in the range of 8.0 to 10.0. Formaldehyde is then added to produce a pH in the range of 5.5 to 7.0. This is followed by addition of sodium or potassium cyanide which causes the pH to increase, but concurrent additions of hydrochloric acid serve to maintain said pH in a range of 7.5 to 9.5. A high pressure liquid chromatography ion exchange may then be carried out to isolate the desired pure N-phosphonomethylglycinonitrile. The several steps of the reaction scheme are conducted at room temperature or below, preferably in the range of 0° to 20° C.

Care should be taken, particularly during the final steps, to maintain the pH within the above-defined limits. A lower pH serves to slow the reaction, thereby decreasing the yield, while a higher pH results in some loss of the product by hydrolysis to the amide.

In order to significantly reduce the presence of unreacted aminomethylphosphonic acid in the desired product, an excess of both formaldehyde and the cyanide can be employed. The formaldehyde can be in 5 to 40% excess with about 20% being preferred. The potassium cyanide can be used in 10 to 150% excess with about 130-140% being preferred.

This process can be employed to prepare the free glycinonitriles, and it can also be employed to prepare the known mono and diesters thereof. The products of said process can be shown by the formula

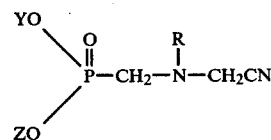

wherein R has the same meaning as above, and Y and Z are independently selected from hydrogen, hydrocarbyl and substituted hydrocarbyl. Preferred mono and diesters are those wherein Y and Z are lower alkyl or phenyl. The salts of the above products are obtained by neutralization with an appropriate base.

The examples which follow will serve to further illustrate the preparation of specific individual compounds of the class described.

EXAMPLE 1

A slurry of 5.6 grams (0.05 mole) of aminomethylphosphonic acid in 25 grams of water (measuring pH 2.6 with an electrode calibrated with pH 8.0 buffer at 20° C.) was stirred and treated at once with 5.0 grams of 50.9% aqueous sodium hydroxide solution. After cooling, the pH was 9.7, and the mixture was a homogeneous solution.

This solution was cooled to 0°–5° C. and treated dropwise with 4.2 grams (0.0525 mole) of 37% aqueous formaldehyde below 10° C. It was then stirred for 30 minutes at 0°–5° C., and the pH measured 6.6 on the temperature compensated meter. To this clear solution, there was added, in small portions and with cooling at 10°–15° C., a solution of 3.6 grams (0.055 mole) of potassium cyanide in 15 grams of water. As the pH increased to 9.0, a total of 2.7 grams of 37% hydrochloric acid was added in small portions to maintain the mixture in the range of pH 8–9. The pH at completion of the addition was 8.0 at 11° C. The cooling bath was removed, and, after 95 minutes, the temperature had risen to 17° C. with the pH at 7.9.

The mixture was allowed to stand for 20 hours at 17°–22° C. after which the pH was 8.7. It was then filtered, and the filtrate was passed through a column of ion exchange resin in the acid form. The approximate flow rate was 5 ml. per minute, and fractions were collected at 4 minute intervals. The early fractions containing hydrochloric acid and other impurities were discarded. Fractions 23–34 were combined and concentrated to dryness in vacuo at 100° C. to give 3.94 grams of a colorless crystalline solid. Fractions 37–50 yielded 1.14 grams of unchanged aminomethylphosphonic acid. Based upon the amount of expended starting material, the yield of the solid was 65%. The solid, N-phosphonomethylglycinonitrile, was recrystallized from hot water and melted, with decomposition, at 178°–180° C. Elemental analysis gave 23.85% carbon, 4.88% hydrogen, 18.55% nitrogen and 20.79% phosphorus as against calculated values of 24.01%, 4.70%, 18.67% and 20.64% respectively for $C_3H_7N_2O_3P$.

EXAMPLE 2

A mixture of 1.60 grams of the product of Example 1 in 30 ml. of water was stirred and cooled to 5°–15° C. Dilute sodium hydroxide solution was added dropwise until the pH was 6.8 measured with an electrode calibrated against a pH 8.0 buffer. The clear solution was rotoevaporated to near dryness at <15° C.

The syrupy residue was dried overnight in a dessicator over potassium hydroxide pellets at below 1 mm. The foamed salt obtained was broken up and redried to give 2.07 grams of a hydrated solid. A sample of this product, the monosodium salt of N-phosphonomethylglycinonitrile in the dihydrate form, was redried at 56° C./<1 mm. and sintered at 138°–160° C. Elemental analysis gave 17.12% carbon, 4.92% hydrogen and 14.57% nitrogen as against calculated values of 17.32%, 4.84% and 13.36% respectively for $C_3H_6NaN_2O_3P.2H_2O$.

EXAMPLE 3

A mixture of 1.60 grams of the product of Example 1 in 20 ml. of water was cooled at 10°–15° C. and titrated to a pH of 6.42 by the dropwise addition of 2-propylamine. The resultant clear, cold solution was rotoevaporated at <15° C., dried over sodium hydroxide pellets in vacuo, broken up and then redried. The solid product, 2.29 grams of the monoisopropylamine salt of N-phosphonomethylglycinonitrile in the hemihydrate form, was redried at 56° C./<1 mm. and appeared to sinter and decompose above 100° C. Elemental analysis gave 33.30% carbon, 7.84% hydrogen and 19.28% nitrogen as against calculated values of 33.02%, 7.86% and 19.25% respectively for $C_6H_{16}N_3O_3P.\frac{1}{2}H_2O$.

EXAMPLE 4

A slurry of 0.29 grams of reagent grade magnesium hydroxide in 30 ml. of water at 0°–10° C. was treated at once with 1.50 grams of the product of Example 1 with stirring. The resultant clear solution of pH 5.8 was then frozen. When the ice was allowed to melt, a crystalline solid which appeared redissolved. Rotoevaporation gave a gum which slowly changed to a powder during further drying. The very light tan product obtained was 1.74 grams of the monomagnesium salt of N-phosphonomethylglycinonitrile in the hemihydrate form. After being redried at 56° C./<1 mm., the powder product sintered at about 95°–105° C., turned yellow and then amber, and further decomposed up to 130° C. Elemental analysis gave 21.63% carbon, 3.87% hydrogen and 16.82% nitrogen as against calculated values of 21.74%, 3.95% and 16.90% respectively for $C_6H_{12}MgN_4O_6P_2.\frac{1}{2}H_2O$.

EXAMPLE 5

A slurry of 5.6 grams of phenyl aminomethylphosphonate in 40 ml. of water was treated with small portions of solid potassium bicarbonate until the pH was 6.0, and it was then diluted with 100 ml. of water. It was cooled to 10° C., treated with 2.7 grams of formalin, stirred for 30 minutes at 15°–20° C., and recooled to 10°–12° C. An aqueous solution of 2.2 grams of potassium cyanide was added in portions along with enough hydrochloric acid to maintain a pH of 7.5. The final pH was 7.3 at 15° C. After standing overnight, the resultant solution was filtered and subjected to ion-exchange chromatography to yield 2.12 grams of O-phenyl N-phosphonomethylglycinonitrile. In addition, another 0.5 gram of product was present in, but not isolated from, impurities including unreacted starting material and aminomethylphosphonic acid. The nmr spectrum of the product was identical to that of the same product prepared as described in U.S. Pat. No. 4,083,898.

EXAMPLE 6

A solution of 8.4 grams of diethyl aminomethylphosphonate in 20 ml. of ethanol was treated with 4.0 grams of formalin, stirred and cooled at 0°–10° C. with a pH of 7.8 at 5° C. There was then added, in small portions, a solution of 3.5 grams of potassium cyanide in 15 ml. of water. The reaction was exothermic to 18° C., and the mixture was cooled to 10°–12° C. Alternating additions of the cyanide solution and hydrochloric acid gave a pH of 7.9 at 10° C. After warming to 15°–20° C. and stirring for 2 hours, the pH was 7.0. Inorganic salts separated upon standing overnight and were removed by filtration. The filtrate was diluted with excess ethanol and rotoevaporated on an aspirator, benzene being added to azeotrope residual water. The product obtained as a colorless oil was 4.1 grams of O,O-diethyl N-phosphonomethylglycinonitrile. Identification of the product was confirmed by comparison of the nmr spectrum with another sample of this known compound described in U.S. Pat. No. 4,008,296.

EXAMPLE 7

The procedure described in Example 1 was followed using 4.2 grams of N-ethyl aminomethylphosphonic acid, 2.6 grams of formalin and 2.2 grams of potassium cyanide in aqueous solution, and the resultant clear solution had a final pH of 7.5. Ion exchange chromatography gave 2.63 grams of product after removal of 0.72 grams of unreacted starting material. Further chromatographic purification gave a cream colored solid which was redried at 100° C./<0.1 mm. The final product obtained as a colorless glass was N-ethyl N-phosphonomethylglycinonitrile in the trihydrate form. The structure of the product was confirmed by nmr and mass spectroscopy. Elemental analysis gave 25.87% carbon, 7.38% hydrogen, 12.07% nitrogen and 13.34% phosphorus as against calculated values of 25.86%, 7.17%, 11.84% and 13.36% respectively for $C_5H_{11}N_2O_3P.3H_2O$.

EXAMPLE 8

A slurry of 5.6 grams (0.05 mole) of aminomethylphosphonic acid in 30 grams of water (measuring pH 1.8 with an electrode calibrated with pH 4.0 buffer) was stirred during dropwise addition of 50% aqueous sodium hydroxide to bring the pH to 9.0. The resultant solution was cooled to 10°-15° C. and stirred during the addition of 4.6 grams (0.0575 mole) of 37% aqueous formaldehyde, bringing the pH to 6.1. It was then further stirred for 60 minutes at about 15° C.

A solution of 7.5 grams (0.115 mole) of potassium cyanide in 20 ml. of water was added in small portions at about 15° C. until the pH rose to 8.5. Dilute hydrochloric acid was added to lower the pH to 8.0. This was followed by alternating additions of the cyanide and the acid with the highest pH being 9.5. When the potassium cyanide had been completely added, the final pH was adjusted to 8.5 at 18° C., and the solution was stirred for 2 hours. The pH was then adjusted to 7.5, and, after standing overnight, it was readjusted to 6.5. The reaction mixture was filtered, and the filtrate obtained was 101.5 grams of dark amber solution. A 22.9 grams portion of the filtrate was passed through a column of ion exchange resin in the acid form to give 1.11 grams of N-phosphonomethylglycinonitrile together with 0.06 gram of unchanged aminomethylphosphonic acid. Calculations based upon the total weight of said filtrate showed the yield of the nitrile to be 65.6% of theory with 4.9% of unchanged acid. A comparison with the results of Example 1 shows that the use of excess formaldehyde and cyanide gave the same yield while reducing the percentage of unchanged acid from 20.4% to 4.9%.

The preparation just described was repeated using 5.6 grams of aminomethylphosphonic acid, 4.8 grams of the formaldehyde and 5.9 grams (0.12 mole) of sodium cyanide. The yield of N-phosphonomethylglycinonitrile was 66.2% while the percentage of unchanged aminomethylphosphonic acid was less than 2.0%.

As noted above, the compounds prepared herein can be converted to a known herbicide, N-phosphonomethylglycine. Such conversion can be accomplished by either acid or alkaline hydrolysis. To illustrate the acid hydrolysis, a solution of 0.9 grams of N-phosphonomethylglycinonitrile in 50 ml. of concentrated hydrochloric acid diluted with 100 ml. of water was boiled gently for 4.5 hours. The solution was concentrated to dryness in vacuo to give 1.5 grams of an off-white solid, and nmr analysis showed the presence of the desired N-phosphonomethylglycine. To remove impurities including ammonium chloride, the solid was dissolved in 15 ml. of water by the dropwise addition of 50% sodium hydroxide, and it was then passed through an ion exchange column in the acid form. Fractions 6-30 which had pH<2 were combined and concentrated to about 15 ml. The addition of 30 ml. of ethanol gave crystals, and 0.72 gram were collected and dried. Fractions 31-60 which had pH 2-5, and the mother liquors, were combined and dried to give a further 0.19 gram for a total yield of 90% of N-phosphonomethylglycine. This product sintered and decomposed at 220°-227° C.

Alkaline hydrolysis was illustrated by gently boiling 1.77 grams of N-phosphonomethylglycinonitrile in a solution of 50% sodium hydroxide in 30 ml. of water for 3.5 hours. After 2 hours, a stream of nitrogen was introduced to remove ammonia. The final pH was about 12, and nmr analysis showed the desired N-phosphonomethylglycine. The solution was then passed through an ion exchange column in the acid form, concentrated, and the product precipitated by adding ethanol. There was obtained 1.66 grams of N-phosphonomethylglycine as white crystals, a yield of 83%.

The post-emergent herbicidal activity of various compounds of this invention is demonstrated as follows. The active ingredients are applied in spray form to 14-21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in greenhouse and the effects are observed and recorded after approximately 2 weeks or approximately 4 weeks. The data is given in Table I.

The post-emergent herbicidal activity index used in Table I is as follows:

| Plant Response | Index |
| --- | --- |
| 0-24% Inhibition | 0 |
| 25-49% Inhibition | 1 |
| 50-74% Inhibition | 2 |
| 75-99% Inhibition | 3 |
| All killed | 4 |

In said Table, the compounds are designated by the Example numbers, WAT indicates weeks after treatment, and the plant species treated are each represented by a code letter as follows:

| | |
| --- | --- |
| A - Canada Thistle | G - Yellow Nutsedge |
| B - Cocklebur | H - Quackgrass |
| c - Velvetleaf | I - Johnsongrass |
| D - Morningglory | J - Downy Brome |
| E - Lambsquarters | K - Barnyardgrass |
| F - Smartweed | |

TABLE I

| Compound | WAT | kg/h | A | B | C | D | E | F | G | H | I | J | K |
|---|---|---|---|---|---|---|---|---|---|---|---|---|---|
| 1* | 2 | 11.2 | 2 | 3 | 3 | 3 | 3 | 3 | 2 | 1 | 1 | 1 | 3 |
|  | 4 | 11.2 | 3 | 3 | 4 | 3 | 3 | 2 | 2 | 1 | 2 | 2 | 3 |
|  | 2 | 5.6 | 3 | 4 | 2 | 2 | 4 | 3 | 1 | 1 | 3 | 1 | 3 |
|  | 4 | 5.6 | 4 | 4 | 2 | 2 | 4 | 4 | 2 | 0 | 2 | 2 | 3 |
| 2 | 2 | 11.2 | 2 | 4 | 3 | 2 | 3 | 4 | 2 | 0 | 3 | 1 | 3 |
|  | 4 | 11.2 | 3 | 4 | 1 | 2 | 4 | 4 | 3 | 1 | 4 | 1 | 3 |
|  | 2 | 5.6 | 1 | 3 | 1 | 1 | 4 | 1 | 1 | 0 | 4 | 0 | 1 |
|  | 4 | 5.6 | 2 | 4 | 0 | 2 | 4 | 1 | 2 | 0 | 4 | 0 | 2 |
| 3 | 2 | 11.2 | 2 | 3 | 1 | 1 | 2 | 4 | 2 | 1 | 3 | 1 | 3 |
|  | 4 | 11.2 | 2 | 4 | 2 | 2 | 2 | 4 | 3 | 1 | 4 | 1 | 4 |
|  | 2 | 5.6 | 1 | 3 | 2 | 1 | 1 | 2 | 0 | 0 | 4 | 1 | 1 |
|  | 4 | 5.6 | 4 | 4 | 2 | 2 | 1 | 2 | 1 | 0 | 4 | 2 | 2 |
| 4* | 2 | 11.2 | 3 | 3 | 3 | 2 | 4 | 4 | 2 | 3 | 4 | 3 | 4 |
|  | 4 | 11.2 | 3 | 4 | 4 | 3 | 4 | 4 | 3 | 4 | 4 | 4 | 4 |
|  | 2 | 5.6 | 3 | 3 | 1 | 2 | 4 | 3 | 2 | 1 | 3 | 2 | 2 |
|  | 4 | 5.6 | 3 | 4 | 0 | 2 | 4 | 4 | 3 | 1 | 4 | 0 | 3 |
| 7 | 4 | 11.2 | 0 | 0 | 0 | 0 | 0 | 0 | 0 | 0 | 0 | 0 | 0 |
| 8** | 2 | 11.2 | 2 | 2 | 2 | 2 | 4 | 4 | 2 | 3 | 3 | 1 | 2 |
|  | 4 | 11.2 | 2 | 3 | 2 | 2 | 4 | 4 | 3 | 4 | 4 | 2 | 3 |

*=These compounds were formulated for spraying immediately prior to application.
**=The material tested from Example 8 was a sample of the crude reaction product taken prior to the ion exchange chromatography.

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amines, long chain acid esters of sodium isethionate, esters of sodium sulfosuccinate, sulfated or sulfonated fatty acids esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acyl)taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powders of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicant and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention effective amounts of the glycinonitrile are applied to above-ground portions of plants. The application of liquid and particulate solid herbicidal compositions to above-ground portions of plants can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where inhibition of the aquatic plants is desired.

The application of an effective amount of the compounds of this invention to the plant is essential and critical for the practice of the present invention. The exact amount of active ingredient to be employed is dependent upon such factors as the plant species and stage of development thereof, and the amount of rainfall as well as the specific compound employed. In foliar treatment for the inhibition of vegetative growth, the active ingredients are applied in amounts from about 0.56 to about 22.4 or more kilograms per hectare. In applications for the inhibition of aquatic plants, the active ingredients are applied in amounts of from about 0.1 parts per million to about 1000 parts per million, based on the aquatic medium. An effective amount for phytotoxic or herbicidal action is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

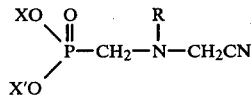

wherein R represents hydrogen, X represents hydrogen and X' represents hydrogen or an herbicidally acceptable cation.

2. The compound as defined in claim 1 wherein X' is hydrogen.

3. A compound as defined in claim 1 wherein X' is sodium.

4. A compound as defined in claim 1 wherein X' is isopropylammonium.

5. A compound as defined in claim 1 wherein X' is ½ magnesium.

6. A herbicidal composition comprising an inert adjuvant and a herbicidally effective amount of a compound of claim 2.

7. A herbicidal composition comprising an inert adjuvant and a herbicially effective amount of a compound of claim 3.

8. A herbicidal composition comprising an inert adjuvant and a herbicidally effective amount of a compound of claim 4.

9. A herbicidal composition comprising an inert adjuvant and a herbicidally effective amount of a compound of claim 5.

10. A herbicidal method which comprises applying to plants a herbicidally effective amount of a compound of claim 2.

11. A herbicidal method which comprises applying to plants a herbicidally effective amount of a compound of claim 3.

12. A herbicidal method which comprises applying to plants a herbicidally effective amount of a compound of claim 4.

13. A herbicidal method which comprises applying to plants a herbicidally effective amount of a compound of claim 5.

14. A process for preparing a compound of the formula

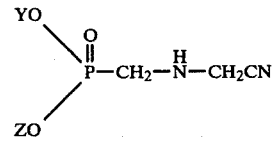

wherein Y and Z are independently selected from hydrogen, lower alkyl and phenyl, which comprises the steps of (a) treating an aminomethylphosphonic acid or ester of the formula

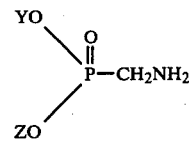

wherein Y and Z have the above meaning, with an alkali metal hydroxide to form a mono salt, (b) adding formaldehyde to an aqueous solution of said salt, (c) adding sodium or potassium cyanide to the solution of (b), steps (a)–(c) being carried out at room temperature or below and the pH of the reaction mixture being maintained in the range of 7.0 to 10.0 during steps (b) and (c), and (d) concentrating or acidifying to obtain said compound.

15. A process as defined in claim 14 wherein Y and Z are hydrogen.

16. A process as defined in claim 14 wherein an excess of both formaldehyde and the cyanide are employed.

17. A process as defined in claim 14 wherein at least one of Y and Z is other than hydrogen.

18. A process as defined in claim 14 wherein the cyanide is potassium cyanide.

19. A process as defined in claim 15 wherein the cyanide is potassium cyanide.

20. A process as defined in claim 16 wherein the cyanide is potassium cyanide.

* * * * *